United States Patent [19]

Heckele

[11] 4,372,295
[45] Feb. 8, 1983

[54] ENDOSCOPES

[75] Inventor: Helmut Heckele, Knittlingen, Fed. Rep. of Germany

[73] Assignee: Richard Wolf GmbH, Knittlingen, Fed. Rep. of Germany

[21] Appl. No.: 151,304

[22] Filed: May 19, 1980

[30] Foreign Application Priority Data

May 25, 1979 [DE] Fed. Rep. of Germany ... 7915282[U]

[51] Int. Cl.³ .............................................. A61B 1/00
[52] U.S. Cl. ......................................... 128/4; 128/6
[58] Field of Search ...................... 128/4, 6, 756, 757, 128/7, 303.15

[56] References Cited

U.S. PATENT DOCUMENTS

| 2,004,559 | 6/1935 | Wappler et al. | 128/303.15 |
| 2,701,559 | 2/1955 | Cooper | 128/757 |
| 4,178,920 | 12/1979 | Cawood, Jr. et al. | 128/6 |

Primary Examiner—Kyle L. Howell
Assistant Examiner—Nancy A. B. Swisher
Attorney, Agent, or Firm—Kinzer, Plyer, Dorn & McEachran

[57] ABSTRACT

This invention relates to endoscopes having a hollow shaft to receive a flexible forceps, probe or the like passed therethrough with the distal end of the forceps or the like projecting from the shaft, and means for pivotally displacing this distal end of the forceps, probe or the like.

According to the invention, two rods pass through the shaft parallel to its longitudinal axis and are joined together into a U-shape at their distal end, the latter being bent over at an angle away from the longitudinal axis of the shaft to bear against the end of the forceps distally projecting from the endoscope shaft when in position. These rods are connected to a slider in the proximal end of the endoscope shaft, and the slider is displaceable parallel to the longitudinal axis of the shaft towards the proximal end against a spring by means of an external handle. The two rods may be joined together at their distal ends directly or by an intermediate web and they may be connected to the slider in a releasable manner.

5 Claims, 3 Drawing Figures

4,372,295

ENDOSCOPES

BACKGROUND OF THE INVENTION

The present invention relates to endoscopes of the kind having a hollow shaft to receive a flexible forceps, probes or the like passed therethrough, with the distal end of said forceps probe or the like projecting from said shaft, and means for pivotally displacing said distal end of said forceps, probe or the like.

In the case of endoscopes, it is known that the distal projecting extremity of flexible ancillary instruments may be pivoted under observation by means of a so-called Albaran lever, to bring the instrument into the field of observation at or close to an object. These or analogous devices for pivoting the far-end portion of flexible ancillary instruments require a comparatively complex structure.

It is therefore an object of the invention to secure a structurally simplified pivoting device for flexible ancillary instruments such as forceps, probes or the like, which are to be passed through the shaft of an endoscope.

SUMMARY OF THE INVENTION

To achieve this and other objects, the invention accordingly consists in an endoscope having a hollow shaft to receive a flexible forceps, probe of the like passed therethrough with the distal end of said forceps or the like projecting from said shaft, and means for pivotally displacing said distal end of said forceps probe or the like wherein two rods pass through said shaft parallel to the longitudinal axis thereof and are joined together into a U-shape at their distal end said distal end of said rods being bent over at an angle away from said axis of said shaft to bear against said end of said forceps distally projecting from said endoscope shaft when in position, said rods being connected to a slider in the proximal end of said endoscope shaft, said slider being displaceable parallel to said longitudinal axis of said shaft towards the proximal end against a spring by means of an external handle.

BRIEF DESCRIPTION OF THE DRAWINGS

In order that the invention may be more clearly understood, reference will now be made to the accompanying drawings which show one embodiment thereof by way of example and in which.

DETAILED DESCRIPTION OF THE PREFERRED EMBODIMENT

Figure 1:
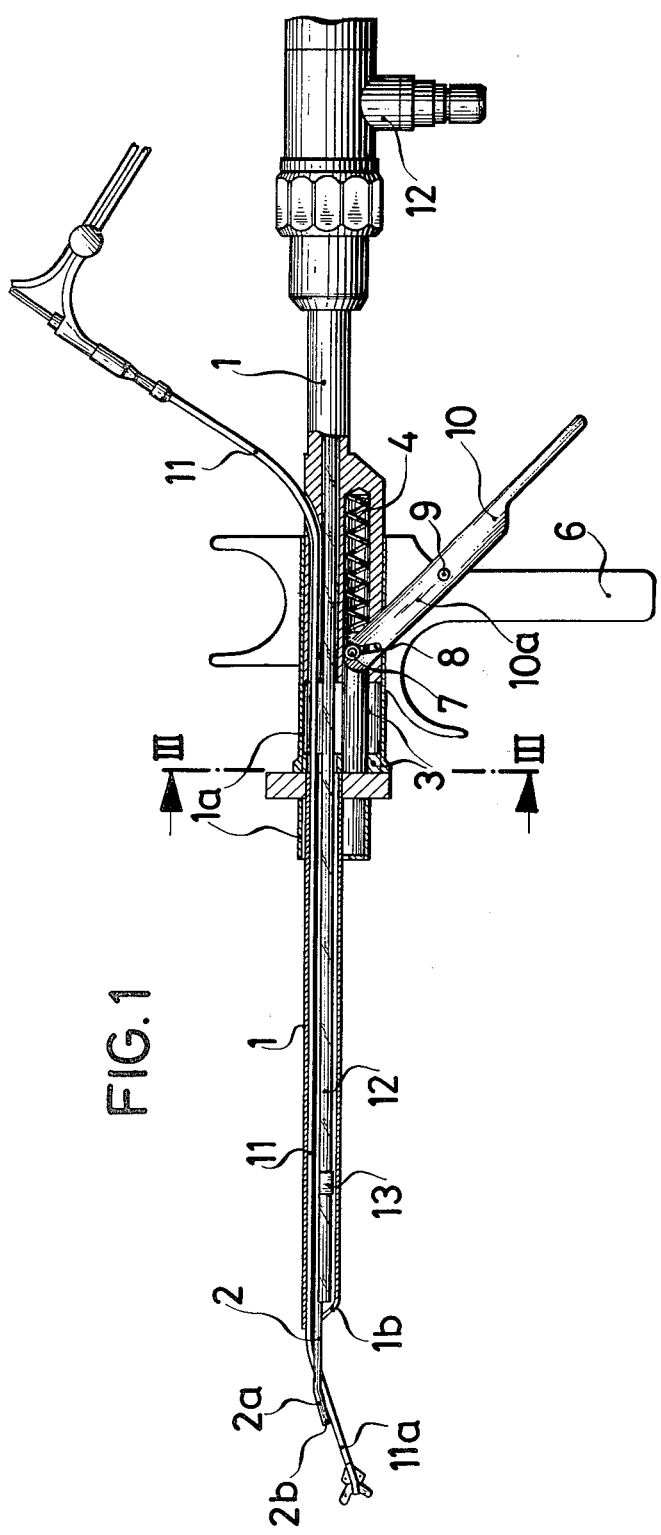
FIG. 1 shows an endoscope, partially in sideview and axial cross-section, through a hollow shaft of which passes a flexible forceps shown in dotted lines.
Figure 3:
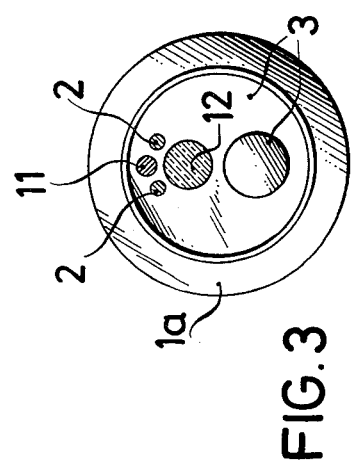
FIG. 3 shows an enlarged diagrammatical cross-section along the line III—III of FIG. 1.

Referring now to the drawings, in accordance with the embodiment shown in the drawings, the endoscope illustrated comprises a hollow shaft 1 the proximal end of which is enlarged at 1a. Passing through the shaft 1 and parallel to the longitudinal axis thereof are two parallel rods 2 which project distally freely from the shaft, the distal portions 2a of said tubes being bent over at an angle and joined together into a U-shape 2b either directly or via a web. The proximal ends of the rods 2 are releasably connected within the enlarged shaft portion 1a to a slider 3 which may be displaced towards the near end against a spring 4. Thanks to the releasable connection, it is possible to vary the angle of the distal portion 2a of the rods between 30° and 90° by keeping a few sets of such rods available. In order to move the slider 3, it is connected to a lateral entraining pin 7 passing through an axially parallel slot 5 of the shaft 1a and of a handle element 6. The free end of pin 7 is engaged in a slot 8 of one arm 10a of a double lever 10 pivotally fitted at 9 on the handle 6, said slot being inclined and extending approximately transversely to the displacement of the slider.

Forceps 11 denoted by dotted lines whose distal end projects out of the shaft 1 in a manner which can be varied by axial displacement of the forceps, are passed through the shaft 1 between the two rods 2. By means of the angled portion 2a of the rods 2, the distal joint 2b of the rod forces the free flexible forceps distal section 11a downwards at an angle, as shown in FIG. 1.

Figure 2:
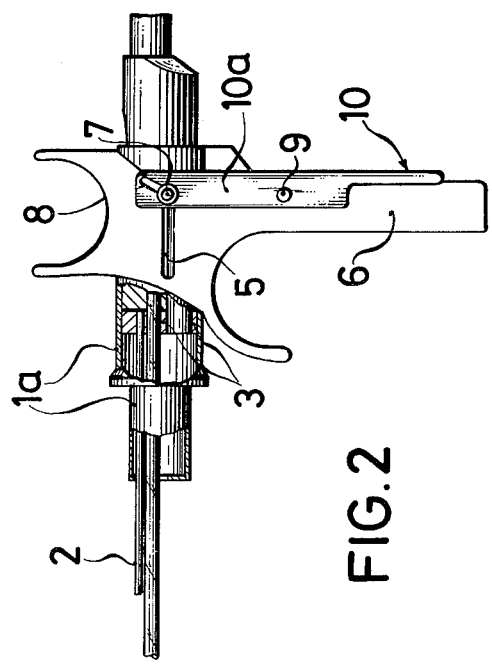
FIG. 2 shows the proximal shaft portion of the endoscope according to FIG. 1 in axial cross-section and with a two-armed handle pivoted from the position of FIG. 1.

If the slider 3 is then placed in the position shown in FIG. 2 by pivotal displacement of the double lever 10, 10a, the slider 3 is displaced towards the proximal end and entrains the rods 2, so that the distal extremity 2b is brought closer to the distal shaft extremity 1b, wherey the flexible forceps section 11a is bent upwards between the two rod portions 2a and the shaft extremity 1b, whereas the distal forceps section 11a thereby acquires an increased angular setting. The angular setting of the distal forceps section 11a is thus adjustable. This adjustment may be observed by means of an optical system 12 which may be passed through the shaft 1.

Thanks to the device described in the foregoing, it is possible to obtain an optional angular setting of the distal section 11a of a flexible ancillary instrument in the simplest manner imaginable, the rods 2 between them determining the position of the flexible forceps 11 and the rods 2 complementarily being connectible to a slotted annular spring 13 which resiliently enflanks the optical system 12 and thereby equally holds the same in position within the shaft. Thanks to the two parallel rods 2, separate guiding passages of the shaft may consequently be omitted.

In the claims:

1. An endoscope having a hollow shaft receiving a flexible ancillary instrument passed therethrough with the distal end of said instrument projecting from the distal end of said shaft, and means for flexibly displacing said distal end of said instrument at different selective angles, wherein said means comprises two rods which pass through said shaft parallel to the longitudinal axis thereof and are joined together into a U-shape at their distal end, said distal end of said rods being bent over at an angle downwardly away from said axis of said shaft to bear against and force downwardly at an angle the upper side of said distal end of said instrument distally projecting from said endoscope shaft when in position, said rods being connected to a slider in the proximal end of said endoscope shaft, said slider being displaceable parallel to said longitudinal axis of said shaft towards the proximal end against a spring by means of an external handle and which displacement of the slider moves said U-shape distal end of the rods closer to the distal end of said shaft along the upper side of the distal end of said instrument, resulting in the distal end of said instrument outward of the distal end of said shaft acquiring an increased angular setting downward.

2. An endoscope according to claim 1, wherein said handle of said slider is constituted by a double-armed level pivotally installed on a handle member projecting from said endoscope.

3. An endoscope according to claim 2, wherein said slider is provided with an entraining pin which projects through axially parallel elongated slots formed in said endoscope shaft and said endoscope handle, said pin also passing through a portions elongated slot formed in one arm of said double-armed lever which extends approximately transversely to the displacement of said slider.

4. An endoscope according to claim 1 and including an optical system extending through said endoscope shaft, wherein said instrument extends within said endoscope shaft between said two rods, said rods being connected to a slotted annular spring which resiliently enflanks said optical system within said endoscope shaft.

5. An endoscope according to claim 1 or 4, wherein said angle of said distal ends of said rods is between 30° and 90°.

* * * * *